United States Patent
McIntyre

(10) Patent No.: US 10,149,988 B2
(45) Date of Patent: Dec. 11, 2018

(54) DETECTION OF DAMAGE TO X-RAY TARGETS IN ELECTRON ACCELERATORS FOR RADIOTHERAPY

(71) Applicant: Varian Medical Systems, Inc., Palo Alto, CA (US)

(72) Inventor: Raymond D. McIntyre, Los Altos Hill, CA (US)

(73) Assignee: Varian Medical Systems, Inc., Palo Alto, CA (US)

(\*) Notice: Subject to any disclaimer, the term of this patent is extended or adjusted under 35 U.S.C. 154(b) by 273 days.

(21) Appl. No.: 15/074,294

(22) Filed: Mar. 18, 2016

(65) Prior Publication Data

US 2017/0266463 A1 Sep. 21, 2017

(51) Int. Cl.
*A61N 5/10* (2006.01)
*H01J 35/08* (2006.01)

(52) U.S. Cl.
CPC ......... *A61N 5/1048* (2013.01); *A61N 5/1077* (2013.01); *H01J 35/08* (2013.01)

(58) Field of Classification Search
CPC ...... A61N 5/10; A61N 5/1048; A61N 5/1077; A61N 5/103; H01J 35/08; A61B 6/58; A61B 6/586
USPC .................................. 378/65, 162, 165, 207
See application file for complete search history.

(56) References Cited

U.S. PATENT DOCUMENTS

2010/0020938 A1\* 1/2010 Koch ..................... H01J 35/14
378/138

\* cited by examiner

*Primary Examiner* — Jurie Yun

(57) ABSTRACT

An x-ray apparatus includes a source configured to generate electrons, a target configured to produce x-rays upon impingement of electrons, and a detector configured to detect electrons penetrating the target or reflected from the incident face of the target, indicative of damage to the target.

19 Claims, 3 Drawing Sheets

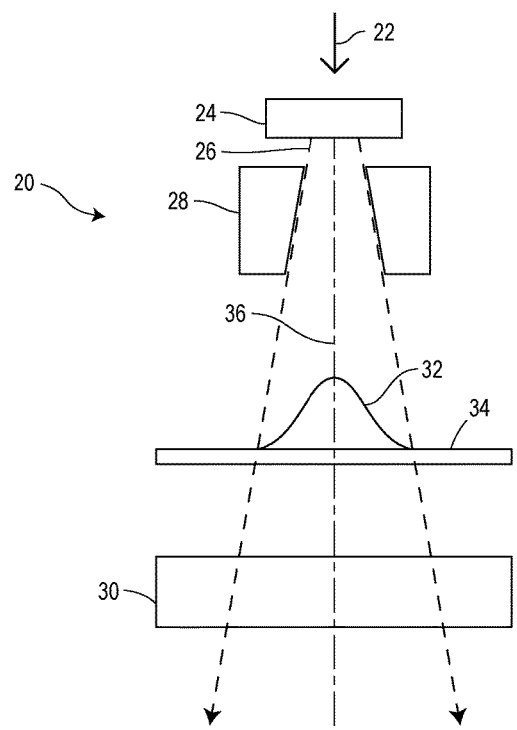
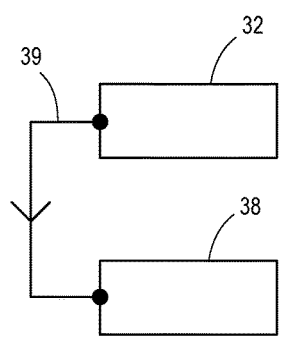
FIG. 2
FIG. 3

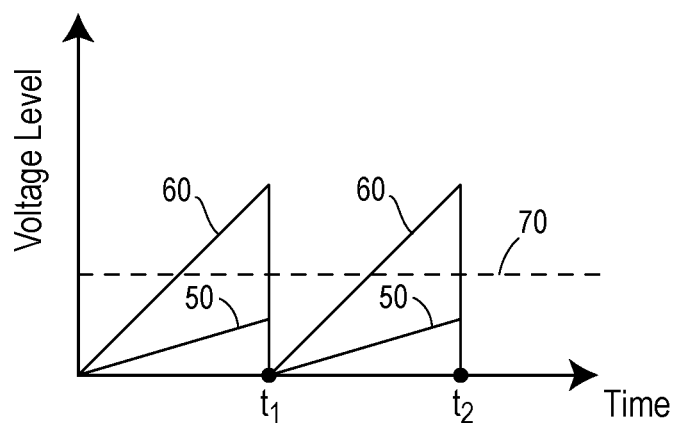
FIG. 4
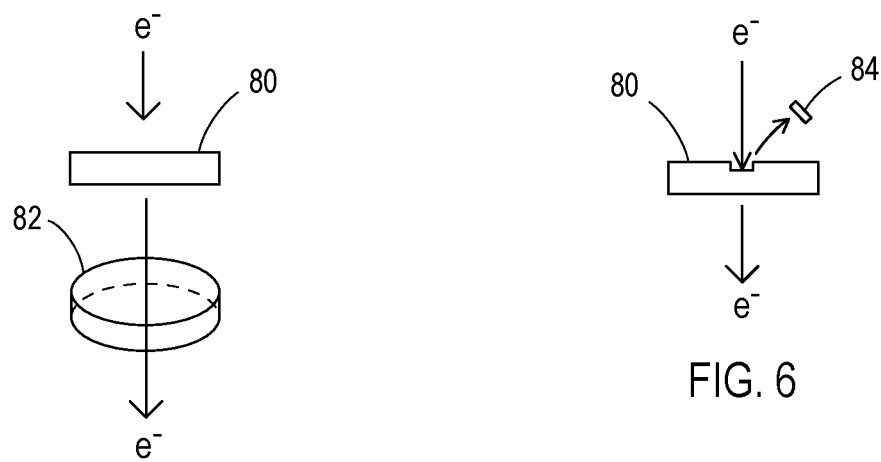
FIG. 5
FIG. 6

DETECTION OF DAMAGE TO X-RAY TARGETS IN ELECTRON ACCELERATORS FOR RADIOTHERAPY

TECHNICAL FIELD

Embodiments of this disclosure relate generally to radiotherapy equipment utilizing high energy electron accelerators. In particular, various embodiments of equipment and methods for detecting damage to x-ray targets in medical accelerators are described.

BACKGROUND

In electron accelerators used for x-ray radiotherapy, a high-energy electron beam is directed on to an electron-to-x-ray conversion target, typically made of a high-density metal or a combination of layers of various metals. Such targets are generally designed for maximal efficiency of x-ray production while not permitting full or over-penetration by the incident electron beam. The targets are typically water-cooled to withstand the thermal stresses induced in the targets by absorption of the power in the electron beam.

However, if the design of or the production process used in manufacturing the target is faulty, then damage of the materials exposed to the electron beam can occur. Such damage is normally progressive and can result in penetration of the target by the incident electron beam, forming a mix of electrons and x-rays in the radiation beam beyond the target. The consequences of this type of target damage, in addition to changing the intended x-ray output, may extend to errors in the accuracy of the radiation therapy dosimetry measurement system and in other monitors of x-ray beam performance.

SUMMARY

This disclosure provides a direct indication of the onset of damage to x-ray targets so that the user of the radiotherapy unit can take appropriate steps to have the target replaced and resume accurate delivery of radiotherapy treatments.

In x-ray therapy, the x-ray beam generated by an x-ray target is typically conditioned by the use of a metal filter to flatten the x-ray beam for treatment purposes. Some x-ray machines provide for the use of a flatness-filter-free (FFF) x-ray beam, as an alternative mode of utilizing the x-ray beam from the target. The flattened or FFF beam then normally passes through an Ionization chamber and certain possible x-ray beam modifiers such as wedges or blocks before being applied to a patient.

According to embodiments of the disclosure, the flattening filter or a simple flat metal plate used with an FFF beam is electrically isolated from the ground to function as an electron collector capable of integrating charge from electrons that may have penetrated the x-ray target. The consequent charge integration will result in voltage increase on the collector. The voltage level on the collector can be measured by remote sensor-electronics and can be set to trigger a 'TARGET WARNING' message at the control console for the radiotherapy unit if the rate of charge exceeds a preset limit at the remote sensor electronics. The collector voltage is arranged to be switched to zero at pre-programmed time intervals. The charge/discharge sequence continues until the x-ray beam is switched OFF. The 'TARGET WARNING' indication will ordinarily continue until the target is replaced.

This summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other embodiments are described in the Detail Description.

BRIEF DESCRIPTION OF THE DRAWINGS

These and various other features and advantages will become better understood upon reading the following detailed description in conjunction with the accompanying drawings and the appended claims provided below, where:

FIG. 2 schematically shows a portion of an x-ray apparatus including the location of an electrically-isolated flattening filter or a FFF plate, either functioning as an electron-charge collector according to embodiments of the disclosure;

FIG. 3 schematically shows a voltage sensor electronic assembly electrically connected to an electron-charge collector according to embodiments of the disclosure;

FIG. 4 is a graph illustrating voltage levels on an electron-charge collector with voltage-level proportional to collected charge and measured in preset time intervals according to embodiments of the disclosure;

FIG. 5 schematically shows measurement of current proportional to leakage electrons from the target using a toroidal current detector according to alternative embodiments of the disclosure; and FIG. 6 schematically shows measurement of electrons reflected by the surface of a target using a secondary emission monitor according to alternative embodiments of the disclosure.

DETAILED DESCRIPTION

Figure 1:
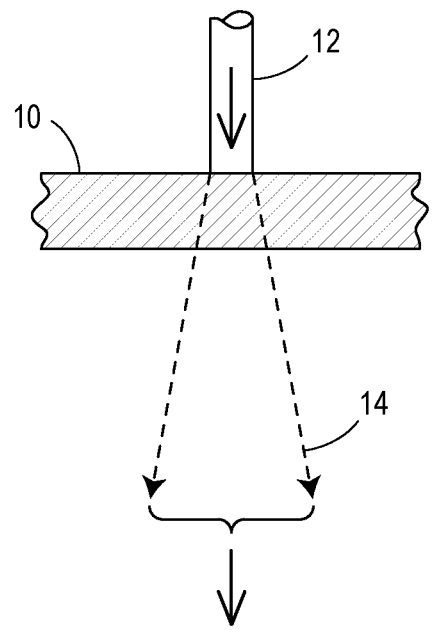
FIG. 1 schematically shows an undamaged target and a damaged target exposed to an incident electron beam for the purpose of producing x-rays.
Figure 1:
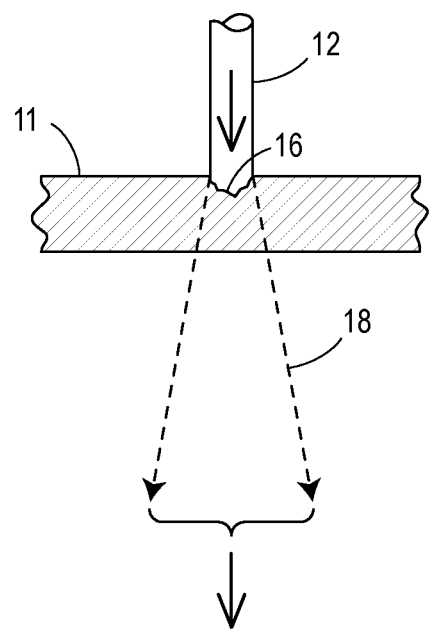

Various embodiments of equipment and methods for detection of damage to x-ray targets are described. It is to be understood that the disclosure is not limited to the particular embodiments described as such. An aspect described in conjunction with a particular embodiment is not necessarily limited to that embodiment and can be practiced in any other embodiments. Further, in the following description, specific details such as examples of specific materials, dimensions, processes, etc. may be set forth in order to provide a thorough understanding of the disclosure. It will be apparent however to one of ordinary skill in the art that some of these specific details may not be employed to practice embodiments of the disclosure. In other instances, well known components or process steps may not be described in detail in order to avoid unnecessarily obscuring the embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise.

An x-ray apparatus is provided. In general, the x-ray apparatus includes a source configured to generate electrons, a target configured to produce x-rays upon impingement by electrons, and a detector configured to detect electrons that have penetrated the target, or have been reflected off the incident face of the target and detected by a secondary emission monitor. Electrons that have penetrated a target or a change in secondary emission from the target may be indications of damage to the target.

In one, or first, embodiment, the detector includes an electron collector configured to integrate charge from the electrons that have penetrated the target and an electrical assembly configured to measure the charge integrated on the electron collector.

In this same embodiment, the x-ray apparatus includes a flattening x-ray filter configured to condition the x-rays produced, and the same flattening filter is electrically isolated from ground and used as an electron collector to integrate the charge from electrons that have penetrated the target.

In this same embodiment, the x-ray apparatus is configured without a flattening filter and in this mode is described as flattening-filter-free or FFF. In this configuration the flattening filter is generally replaced by a flat metal plate. In this embodiment, the flat metal plate would be electrically isolated from ground and be used as a collector of electrons that have penetrated the target.

In this same embodiment, the x-ray apparatus may include either or both a metal flattening x-ray filter and a flat FFF mode metal plate. In either x-ray mode of operation the flattening filter or the FFF-mode plate function as collectors of electrons that have penetrated the target.

In the same embodiment, an electrical assembly is electrically connected to the electron collector, and includes a voltage sensor configured to measure a voltage level established by the charge integrated on the electron collector.

In the same embodiment, the electrical assembly is remotely located and electrically connected to the electron collector via one or more electrical contacts located at the electron collector.

In the same embodiment, the remote electrical assembly is configured to provide a warning signal at the radiotherapy Control Console, of damage to the target when the voltage level from the electron collector reaches a predetermined value.

In a separate, or second, embodiment, the detector of leakage electrons from the target comprises a toroidal current monitor placed below the target to measure the magnitude of the current proportional to electron leakage. The toroidal current detector is electrically connected to a remote electrical assembly that issues a warning signal via the radiotherapy Control Console about damage to the target when the level of the current detected by the toroidal monitor reaches a predetermined value.

In another separate, or third, embodiment, the detector includes a secondary emission monitor configured to collect electrons reflected by a surface of the target. The level of electrons reflected by the surface of a target will be an indication of the extent of damage to the target. The secondary emission monitor is electrically connected to a remote electrical assembly that issues a warning signal via the radiotherapy Control Console about damage to the target when the level of electrons collected by the secondary emission monitor reaches a predetermined value.

In all embodiments, as described, a method of detecting damage to an x-ray target is provided. An electron beam is directed on to an x-ray target, in order to generate an x-ray beam for radiotherapy. Electrons penetrating the x-ray target will generally be an indication of a damaged target.

In a first embodiment, detection of damage comprises integrating the charge accumulated on an electron-collector placed below the target.

In this same embodiment, the collector charge is electrically connected to a remote electrical assembly that converts the charge to a voltage level that is programmed to issue a warning signal that the target is damaged when the voltage level exceeds a pre-determined level.

In a second embodiment, the detecting step includes measuring a current level by a toroidal current monitor placed below the target in order to measure the level of electrons that have penetrated the target. The voltage signal from the toroid is electrically connected to a remote electrical assembly that issues a warning signal that the target is damaged when the voltage level exceeds a pre-determined level.

In a third embodiment, the detecting step includes measuring electrons reflected by the surface of the x-ray target exposed to the incident electron beam, which may be an indication of damage to the target. The voltage signal from the secondary-emission monitor is electrically connected to a remote electrical assembly that issues a warning signal that the target is damaged when the voltage level exceeds a pre-determined level.

Embodiments of the disclosure will now be described with reference to the figures. It should be noted that some figures are not necessarily drawn to scale. The figures are only intended to facilitate the description of specific embodiments, and are not intended as an exhaustive description or as a limitation on the scope of the disclosure.

FIG. 1 schematically shows an undamaged target 10 and a damaged target 11 impinged by an incident electron beam 12 in producing x-rays. As shown, target 10 or 11 can be a transmission-type of target. Alternatively, the principles of the disclosure described herein are also applicable to reflection-type of targets. The target 10 or 11 can be made of a high-density metal such as tungsten or a combination of various metals. The target 10 or 11 is generally designed for high efficiency of x-ray production while not permitting penetration by the incident electron beam. The target 10 or 11 can be cooled by a coolant such as water in operation to withstand the thermal stresses induced in the target by absorption of the power in the incident electron beam, which may have an energy level in the megavoltage range. U.S. Pat. No. 7,831,021 assigned to the same assignee of this application describes various target assemblies for x-ray production, the disclosure of which is incorporated herein by reference in its entirety.

Referring to FIG. 1, when an incident electron beam 12 is directed on to the undamaged target 10, the electrons interact with the target material and x-rays are produced. The produced x-rays transmit through the target 10, forming an output x-ray beam 14, which contains no electrons from the incident electron beam or a negligible amount of electrons.

Damage to a target can occur if the design of or the production process used in manufacture of the target is faulty, and such damage is normally progressive. FIG. 1 schematically shows a damaged target 11 having an eroded region 16. When the incident electron beam 12 is directed on to the eroded region 16 of the damaged target 11, a portion of the incident electrons may penetrate the target 11. As a result, the output radiation beam 18 contains a mix of x-rays and electrons. The electrons in the radiation beam 18 may change the intended x-ray output and also cause errors in treatment dosimetry measurement system and in other monitors of x-ray beam performance. Therefore, it would be desirable to detect any damage to x-ray targets so that the user of the radiotherapy apparatus can take appropriate steps to have the target replaced and resume accurate delivery of radiotherapy treatments.

FIG. 2 schematically shows a portion of an x-ray apparatus 20 including a mechanism for detection of damage to x-ray targets according to embodiments of the disclosure. The x-ray apparatus 20 includes an electron source (not shown) operable to generate an electron beam 22 e.g. in the megavoltage level, an x-ray target 24 configured to produce x-rays 26 upon impingement by electrons, a primary collimator 28 configured to generally limit the extent of the produced x-ray beam 26 from the target 24, and an ion chamber 30 for monitoring the parameters of the x-ray beam 26. For clarity and to focus on description of embodiments of this disclosure, some components or devices which may be included in the x-ray apparatus 20 are not shown or described in detail. Such components or devices may include a field light assembly, movable collimation jaws, multileaf collimator, wedges, shielding blocks, a gantry enclosing and supporting various devices and components, and so on. The x-ray apparatus 20 may be a linear accelerator useful for radiotherapy of patients, or other types of high energy x-ray machines useful in security inspection, medical imaging, scientific research, and so on.

According to embodiments of the disclosure, the x-ray apparatus 20 may include a flattening x-ray filter 32 configured to condition the x-ray beam 26 produced. The flattening photon filter 32 is generally constructed from metal or a combination of metals, and is shaped to "flatten" the forward-peaked x-ray beam, providing a beam with a flattened intensity distribution across the x-ray field. The flattening x-ray filter 32 may be supported by a body member 34, which may be moved, e.g. rotated and/or translated, in positioning the flattening filter 32 relative to the x-ray beam center-line 36.

In some alternative embodiments, the x-ray apparatus 20 may not include any flattening x-ray filter, to take the advantage of the high intensity of the central portion of the output x-ray beam. As such, the x-ray apparatus is flattening-filter-free (FFF). In an x-ray apparatus free of a flattening x-ray filter, a flat metal plate is typically used as a secondary protection measure in case a primary interlock protection mechanism fails in which case an electron beam of high energy intended for x-ray production is accidentally chosen for treatment of patient. The metal plate would attenuate the high energy electron beam intended for x-ray production, thus reducing the risk of danger to the patient in the event that the primary interlock protection mechanism fails.

In some embodiments, the x-ray apparatus may include a flattening x-ray filter, but is operable in either this mode or in an FFF mode. For example, referring to FIG. 2 which shows an x-ray apparatus 20 including a flattening x-ray filter 32, the supporting body member 34 may be provided with two ports, with the flattening filter 32 located and secured in one of the two ports, with the second port being covered by a flat metal plate as a secondary protection measure as described above. In the case of selectable flattening filters to be utilized with different x-ray energies available from the same radiotherapy unit, the selected x-ray filter or FFF plate is positioned in place at the central beam-line 36 by programmed and interlocked movement of the supporting body member 34. U.S. Pat. No. 8,077,830 assigned to the same assignee of this application describes various beam filter positioning devices, the disclosure of which is incorporated herein by reference in its entirety.

According to embodiments of the disclosure, the flattening x-ray filter 32, or the metal plate used with an FFF beam, can be configured to function as an electron collector capable of integrating charge from electrons that may have penetrated the target 24. For ease of description, the term "electron collector" or "collector" is used in the appended claims and the specification to refer to either a flattening x-ray filter, or a metal plate used with an FFF beam, or any other member that is capable of integrating charge of electrons penetrating an x-ray target. The collector such as the flattening filter 32 or the metal plate used with an FFF beam is insulated from ground in order to accumulate the charge from electrons that have penetrated the target 24. By way of example, ceramic or radiation-hard plastic screws, spacers, pins, bolts or the like may be used to secure the flattening photon filter 32 or the metal plate to the supporting body member 34 to allow the electron collector to be insulated from the ground. Electrical contacts (not shown) can be provided in the periphery of the flattening filter 32 or the FFF metal plate for connecting the collector to a remote electrical assembly, for measuring the charge integrated on the collector, as will be described in greater detail below. One advantage of using a flattening x-ray filter or FFF flat metal plate as an electron collector is that existing mounting schemes and structures in an x-ray apparatus can be used so that no major modification to the x-ray machine is required.

The charge integrated on the flattening filter 32 or FFF metal plate can be measured using various methods. As an example, the integrated charge can be measured by measuring the voltage on the collector. Charge integration would result in voltage increase on the collector. The voltage level on the collector can be measured using a remote electrical assembly containing sensor electronics that measure the integrated charge from the collector. FIG. 3 schematically shows a collector 32 and an electrical assembly 38 electrically connected to the collector 32 for measuring the charge integrated on the collector 32 according to embodiments of the disclosure. The electrical assembly 38 may be remotely located outside the x-ray Head Assembly enclosing the electron collector 32. The electrical assembly 38 may be connected by a shielded wire 39 to the collector 32 via contacts provided e.g. on the periphery of the flattening filter 32 or FFF metal plate.

The circuitry or structure of the charge sensor electronics 38 is well known in the art and therefore its detailed description is omitted herein in order to focus on the description of embodiments of this disclosure. In general, within a treatment time, when the target 24 is impinged by an electron beam 22 in producing x-rays 26 (FIG. 2), the charge sensor electronic circuit 38 measures any charge from the collector 32 and converts this to a voltage level proportional to the collected charge on the collector 32. In preset time intervals, measurements are made and voltage levels on the collector 32 may be observed due to the integration of charge of electrons penetrating the target 24. At the end of each time interval, the accumulated charge on the collector 32 is discharged and this process is repeated in subsequent time intervals. The charge and discharge sequence may continue until the treatment ends with the x-ray beam switched off. The electronic circuit 38 is set to trigger a warning signal if the voltage level in each charge-cycle exceeds a predetermined limit, as will be described in greater detail below.

The voltage signals measured by the sensor electronics 38 are schematically illustrated in FIG. 4, where voltage level, proportional to accumulated charge from the collector, is plotted against time, within preset time intervals. Lines 50 represent voltage ramps for a target with minor damage. Lines 60 represent voltage ramps for a target with relatively major damage. In FIG. 4, line 70 represents a preset voltage limit, beyond which a "TARGET WARNING" signal will be triggered and sent to a control station for the radiotherapy unit. The preset voltage limit 70 triggering the "TARGET WARNING" signal is predetermined by the radiotherapy unit manufacturer, based on various factors. Including analysis and tests with targets, and the consequent effects of damage. The "TARGET WARNING" signal will continue with each x-ray treatment, until the target is replaced.

Damage to x-ray targets is normally progressive. One advantage of the disclosure is that such progressive damage to a target can be monitored and steps taken to plan replacement of the target before the damage effects the operational specifications for the radiotherapy unit.

FIG. 5 shows an alternative embodiment for detecting electrons penetrating an x-ray target 80. Instead of using a collector to integrate charge of electrons that have penetrated the target and voltage sensor electronics to measure the voltage level on the collector as illustrated in FIGS. 2 and 3 and described above, the alternative embodiment shown in FIG. 5 uses a toroidal current detector 82 to detect leakage electrons that have penetrated through the target 80. Toroidal current detectors are well known in the art and therefore their detailed description is omitted herein. In general, a toroidal current detector includes a toroidally shaped ring that functions as a magnetic sensor of electric current that passes through the central section of the ring. As shown in FIG. 5, the toroidal current detector 82 may be placed directly below the target 80 to facilitate the detection of electrons that have penetrated the target 80. To introduce a toroidal current detector to an existing x-ray machine, changes to the hardware layout of the treatment head of the x-ray machine will have to be made to accommodate the toroid detector. This may incur significant retrofit costs and machine downtime. Another consideration in using a toroidal current detector to detect leakage electrons is the likelihood of decreased signal-to-noise ratio compared to the embodiment utilizing integrated charge on a collector.

FIG. 6 shows a further alternative embodiment for detecting damage to x-ray targets. Instead of using a collector integrating the charge from electrons that have penetrated through the target as illustrated in FIGS. 2 and 3 and described above, the alternative embodiment shown in FIG. 6 uses a secondary emission monitor (SEM) 84 to detect electrons that are reflected off the surface of the x-ray target 80. The percentage of primary electrons that are reflected off from the surface of the x-ray target 80 is an indication of normalcy of an x-ray target. A damaged or eroded x-ray target would reflect more electrons incident on to the target. By detecting the reflected electrons and calculating the differential of reflection percentages between a target without damage and a target that is undergoing damage, a warning signal will be issued upon detection of unacceptable damage. Similar to the alternative embodiment shown in FIG. 5, the introduction of a secondary emission monitor into an existing x-ray machine will require changes to the hardware layout of the treatment head of the x-ray machine, which will incur significantly increased retrofit costs and machine downtime in addition to decreased signal-to-noise ratio, compared to the embodiment utilizing integrated charge on a collector.

Various methods for detecting damage to x-ray targets in radiotherapy accelerators have been described. Those skilled in the art will appreciate that various other modifications may be made within the spirit and scope of the invention. For example, while a flattening x-ray filter or FFF flat metal plate can be used as an electron collector so that existing mounting schemes and structures in an x-ray apparatus can be used and no major modification to the x-ray machine is required, a dedicated electron collector may be placed on top of the existing flattening filter or the FFF flat metal plate. Furthermore, an x-ray apparatus may include an electron shield or x-ray shield surrounding the chamber to catch electrons and/or x-rays that bounce off from the target. The electron shield can be configured or used as an electron collector. All these or other variations and modifications are contemplated by the inventors and within the scope of the invention.

What is claimed is:

1. An apparatus, comprising:
a source generating electrons;
a target producing x-rays upon impingement by electrons; and
a detector measuring electrons that have penetrated the target to detect damage to the target.

2. The apparatus of claim 1, wherein the detector comprises an electron collector that collects charge from electrons penetrating the target and an electrical assembly measuring the charge collected on the electron collector.

3. The apparatus of claim 2, further comprising an electrically insulated flattening x-ray filter conditioning the x-rays produced, wherein the electron collector comprises the electrically insulated flattening x-ray filter collecting the charge from the electrons penetrating the target.

4. The apparatus of claim 2, further comprising an electrically insulated flattening-filter-free (FFF) metal plate capable of attenuating electrons generated by the source, wherein the electron collector comprises the electrically insulated FFF metal plate collecting the charge from electrons that have penetrated the target.

5. The apparatus of claim 2, further comprising an electrically insulated flattening x-ray filter for conditioning the x-rays produced and an electrically insulated generally flat metal plate capable of attenuating electrons generated by the source, wherein the electron collector comprises the electrically insulated flattening x-ray filter or the electrically insulated and generally flat metal plate, collecting the charge from electrons that have penetrated the target.

6. The apparatus of claim 2, wherein the electrical assembly comprises a voltage sensor measuring a voltage level established by the charge collected on the electron collector.

7. The apparatus of claim 6, wherein the electrical assembly is remotely located and electrically coupled to the electron collector via one or more electrical contacts on the electron collector.

8. The apparatus of claim 6, further comprising a control circuit coupled with the detector, the control circuit providing a warning signal about damage to the target when the voltage level on the electron collector reaches a predetermined value.

9. The apparatus of claim 1, wherein the detector comprises a toroidal current detector measuring a current caused by the electrons penetrating the target passing through the toroidal current detector.

10. The apparatus of claim 9, further comprising a control circuit coupled with the toroidal current detector, the control circuit providing a warning signal about damage to the target when a level of the current detected by the toroidal current detector reaches a predetermined value.

11. An apparatus, comprising:
a source configured to generate electrons;
a target configured to produce x-rays upon impingement by electrons;
a detector configured to measure electrons that have reflected from an incident face of the target; and
a control circuit coupled with the detector, the control circuit providing a warning signal about damage to the target when a level of electrons measured by the detector reaches a predetermined value.

12. The apparatus of claim 11, wherein the detector comprises a secondary emission monitor configured to collect electrons reflected by the incident face of the target, said collected electrons being indicative of an amount of damage to the target.

13. A method, comprising:
generating an electron beam;
directing the electron beam on to an x-ray target, thereby producing x-rays upon impingement of the electron beam on the x-ray target; and
detecting electrons penetrating the x-ray target indicative of damage to the x-ray target.

14. The method of claim 13, wherein the detecting step comprises integrating charge of the electrons penetrating the x-ray target by an electron collector, and measuring the charge integrated.

15. The method of claim 14, wherein the measuring step comprises measuring a voltage level established by the charge integrated on the electron collector.

16. The method of claim 15, further comprising providing a warning signal about damage to the x-ray target when the integrated charge and voltage level measured reaches a predetermined value.

17. The method of claim 13, wherein the detecting step comprises measuring a current by a toroidal current detector caused by the electrons penetrating the x-ray target passing through the toroidal current detector.

18. The method of claim 17, further comprising providing a warning signal about damage to the x-ray target when a level of the current measured reaches a predetermined value.

19. A method, comprising:
generating an electron beam;
directing the electron beam on to an x-ray target, thereby producing x-rays upon impingement of the electron beam on the x-ray target;
measuring electrons reflected from an incident face of the x-ray target indicative of damage to the x-ray target; and
providing a warning signal about damage to the x-ray target when the reflected electrons measured reaches a predetermined value.

* * * * *